United States Patent
Powell et al.

(10) Patent No.: US 8,765,452 B1
(45) Date of Patent: Jul. 1, 2014

(54) FLOW TUBE REACTOR

(71) Applicant: Colorado Energy Research Technologies, Littleton, CO (US)

(72) Inventors: Wayne J. Powell, Centennial, CO (US); Robert D. Boehmer, Centennial, CO (US); Lee L. Johnson, Littleton, CO (US); Ken Swartz, Denver, CO (US); Donald E. Lenci, Boyton Beach, FL (US)

(73) Assignee: Colorado Energy Research Technologies, LLC, Englewood, CO (US)

( * ) Notice: Subject to any disclaimer, the term of this patent is extended or adjusted under 35 U.S.C. 154(b) by 0 days.

(21) Appl. No.: 13/727,226

(22) Filed: Dec. 26, 2012

(51) Int. Cl.
*C12M 1/42* (2006.01)
*C12N 13/00* (2006.01)

(52) U.S. Cl.
USPC ................ 435/285.2; 435/173.8; 435/295.1

(58) Field of Classification Search
USPC ............... 435/173.5–173.8, 295.1, 295.2; 204/409, 411, 660, 663; 205/701, 744, 205/755
See application file for complete search history.

(56) References Cited

U.S. PATENT DOCUMENTS 8,314,231 B2 11/2012 Baures et al.
8,569,050 B1 * 10/2013 Ericsson .................... 435/292.1
2008/0131947 A1 6/2008 Wicking
2008/0311639 A1 12/2008 Navapanich
2012/0052543 A1 3/2012 Yoon
2012/0100577 A1 4/2012 Medoff et al.

FOREIGN PATENT DOCUMENTS

DE 102010007164 A1 * 8/2011
EP 41373 A1 * 12/1981
JP 05245494 A * 9/1993

OTHER PUBLICATIONS

English language machine translation of DE10210100007164 (Aug. 11, 2011), 16 pages.*
English language machine translationof JP 05-245494 (Sep. 24, 1993), 3 pages.*
Banas, T., "The Effects of Ultraviolet Radiation on Yeast", eHow.com, http://www.ehow.com/list_6375291_effects-ultraviolet-radiation-yeast.html, screen capture Dec. 26, 2012.
Hunt, R.W. et al., "Electromagnetic Biostimulation of Living Cultures for Biotechnology, Biofuel and Bioenergy Applications", International Journal of Molecular Sciences, vol. 10, pp. 4515-4558, 2009.
Kohl, A., "What Is the Effect of UV Light on Yeast?", eHow.com, http://www.ehow.com/about_6506247_effect-uv-light-yeast_.html#ixzz259HXnucY, screen capture Dec. 26, 2012.

* cited by examiner

Primary Examiner — William H Beisner
(74) Attorney, Agent, or Firm — Fish & Tsang LLP

(57) ABSTRACT

Devices, systems and methods for increasing fermentation rates of microbes via biostimulation are provided. Electrodes are preferably positioned along an interior or exterior of a tube-shaped component to administer electromagnetic/electric pulses to a solution comprising a microbe. Systems can advantageously be used in new biofuels production plants, or in existing biofuels production plants without the need for significant retrofits.

25 Claims, 7 Drawing Sheets

FLOW TUBE REACTOR

FIELD OF THE INVENTION

The field of the invention is fermentation.

BACKGROUND

The following description includes information that may be useful in understanding the present invention. It is not an admission that any of the information provided herein is prior art or relevant to the presently claimed invention, or that any publication specifically or implicitly referenced is prior art.

With declining global petroleum production, renewable bioenergy (e.g., biofuel) may be needed to sustain and generate economic growth. Bioenergy can be derived from biological sources via fermentation (enzymatic decomposition and utilization of carbohydrates, etc., by microbes). Unfortunately, it can take many hours for a microbe to ferment.

Various factors can affect the rate of fermentation in yeast cells and other microbes. These factors include the type of carbohydrate (rate of $CO_2$ production), concentration of carbohydrate, concentration of salt, osmolarity (total concentration of sugars or salts in the fermentation solution), ethanol concentration, pH, and temperature, among others.

Some have experimented with methods of increasing fermentation rates (i.e., growth and metabolism rates), but have apparently failed to increase growth/metabolic rates by more than a modest amount. Some prior experiments relate to electromagnetic biostimulation. See e.g., *Electromagnetic Biostimulation of Living Cultures for Biotechnology, Biofuel and Bioenergy Applications*, by Ryan W. Hunt et al., *Int. J. Mol. Sci.* 2009, 10, 4515-4558; doi:10.3390/ijms10104515. Unfortunately, Hunt et al. and others apparently fail to teach, motivate or suggest an apparatus, systems or methods of bioelectromagnetic stimulation of microbes for production of biofuels or bioenergy on a commercial scale.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved apparatus, systems and methods of biostimulation of microorganisms to increase their fermentation rates for production of bioenergy.

SUMMARY OF THE INVENTION

The inventive subject matter provides apparatus, systems and methods in which a device is configured to achieve increases in fermentation rates of microorganisms via biostimulation (e.g., bio electromagnetic stimulation). A device or system of the inventive subject matter can advantageously be used in existing biofuels production plants without the need for significant retrofits, and be configured to decrease the time required for complete fermentation of a bioorganism by at least 10%, at least 100%, at least 500%, or even 1,000% or more. For example, it is contemplated that the time required for fermentation of a strain of yeast can be cut from 20-30 hours, to approximately 2-3 hours.

In one aspect of the inventive subject matter, a flow tube reactor system facilitates fermentation of a solution by a microbe within a bioreactor, and comprises a Rapid Fermentation Reactor ("RFR"). A RFR generally comprises a lumen having a suitable length (e.g., at least 0.1 meter, at least 0.5 meter, or even 1 or more meters), and a suitable inner diameter (e.g., at least 1 centimeter, at least 2 centimeters, or even 10 or more centimeters).

Electromagnetic/electric Pulses ("EPs") can be produced via at least two electrodes disposed along an interior or exterior length of the RFR. In some embodiments the electrodes can be spaced along an interior or exterior length of the RFR with regular or irregular spacing (e.g., a phi spacing, a spacing approximating a phi spacing, etc.).

In another aspect of the inventive subject matter, at least four of a plurality of electrodes can have a progressively greater inter-electrode spacing along an interior or exterior length of the RFR.

Pulse driving circuitry can be provided and configured to drive an EP to the electrodes. The pulse can comprise a high voltage pulse having a frequency of at least 10 kHz, at least 20 kHz, at least 500 kHz, or any other suitable frequency configured to accommodate or be advantageous to the growth/metabolism of a microorganism present in a solution (e.g., a liquid, a slurry, any other fluid, etc.).

It is contemplated that each system or component thereof (e.g., RFR, electrode, rectification cell, etc.) can have a duty cycle of between 0.01 to 5%, more preferably 0.01 to 0.1%. As used herein, a "duty cycle" means a percentage of time that a system or device is actively working, compared to the time the system or device is off or resting. For example, where a rectification cell is actively driving a pulse 20% of the time, the rectification cell has a duty cycle of 20%. Similarly, if the rectification cell is actively driving a pulse only 5% of the time, the rectification cell has a duty cycle of 5%.

A system of the inventive subject matter can have non-pulsing periods of at least 0.1, at least 1, at least 5, at least 10, or at least 15 or more minutes between each pulse. A rectification cell or other pulse driving circuitry can be configured to deliver pulses of at least 400, at least 500, at least 600, or even at least 800 or more Volts/cm (V/cm).

Methods of fermenting a fluid to produce a product can include placing a device, system or component (e.g., RFR) of the inventive subject matter into a bioreactor operating upon a microbe containing solution. Methods can also comprise operating the device or system such that a portion of the solution flows through at least a portion of a RFR component, which provides electromagnetic/electric pulses to the solution flowing therethrough.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
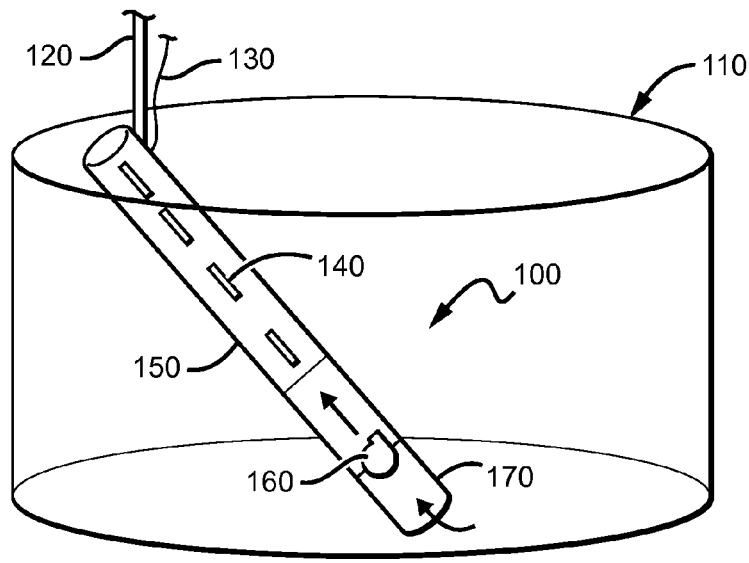
FIG. 1 is a schematic of an embodiment of a device of the inventive subject matter situated inside a fermentation tank.

FIG. 1 is a schematic of a RFR 170, pulse driving circuitry 150 and pump 160 of the inventive subject matter, situated inside a fermentation tank 110. In this embodiment, the RFR 170 comprises a flow tube reactor coupled with a pump 160. However, a RFR 170 can have any suitable form factor, preferably configured as a tube with a lumen. As used herein, a "pulse probe" and a "flow tube reactor" are types of RFR.

The fluid pump 160 coupled with the flow tube reactor of FIG. 1 is configured to direct a flow of a fluid (e.g., a solution comprising a microbe and a carbohydrate) from one portion of the reactor to another. Electrodes 140 are provided along an interior length of the reactor, which are configured to administer EPs driven by a pulse driving circuitry 150. The circuitry 150 can be coupled to a power supply configured to supply power to the circuitry via wires 130. Circuitry 150 can also be coupled to control(s) configured to allow an operator to adjust at least one of the voltage of a pulse, duration of a pulse, and a period between pulses.

The term "pulse driving circuitry" should be interpreted broadly to include, for example, any component comprising two or more contacts configured to create an adjustable spark gap between them. It is contemplated that a spark gap can be adjusted by changing the distance between the at least two contacts via one or more controls. The "pulse driving circuitry" may also be referred to herein from time to time as a "rectification cell" or "pulse circuitry".

Contemplated RFRs (and other components of a device of the inventive subject matter) can be suspended via a bracket (e.g., 120) or other mechanism, either within or outside a fermentation tank (e.g., 110), algae pond or other bioreactor. Moreover, each component of the device can comprise any size and shape suitable for use with a new or existing bioreactor.

Devices and systems of the inventive subject matter can be configured to administer two or more Electromagnetic Pulses ("EPs") either continuously, or at predetermined or random intervals. Some EPs are administered for less than 1 second, less than 1/10 of a second or even less than 1/100 of a second. Moreover, some EPs are only administered less than 50, less than 25, less than 10, or even less than 5 times an hour.

One possible form of EP can include a short-duration, direct current, high-voltage pulse. For example, a pulse length can be between 25 to 130 milliseconds, with voltage ranging from 300 to 4,000 V/cm DC. Very high efficacy has been found with a pulse length of around 70 milliseconds and voltages of approximately 900 V/cm.

The pulse shape can comprise a square wave, sine wave, a saw-tooth wave or any other suitable shape. Resting periods between two pulses can range from less than one minute to over twenty minutes, and preferably between approximately eight and twelve minutes.

The EP(s) can be generated by pulse driving circuitry (e.g., 150), and utilized in a tube or tube-like RFR (e.g., 170). The circuitry can compose or be coupled to the device, a power supply, and one or more controls. An EP of correct frequency and resting period generated by circuitry of the inventive subject matter has been shown to shorten the S-curve growth pattern of some microorganisms (e.g., yeast) by over 50%. In other words, the microorganism's growth/metabolic rates have been increased by approximately 150% or even more.

In some embodiments, a variable pump (e.g., 160) can be provided that allows adjustment of flow rates and flow direction (e.g., from top to bottom, from one end to another end, etc.). Variable pumps can be variable displacement pumps and/or variable speed pumps. Pump sizes and capacities can be preferably selected relative to the size of the bioreactor with which it is used. EPs can be synchronized to the variable flow rate in order to maximize stimulation of an organism in the bioreactor. When appropriate, two or more devices can be used in conjunction with a single bioreactor. Thus, increased biological production can be achieved over a wide variety of bioreactor sizes using a device(s) of the inventive subject matter.

It is also contemplated that a device of the inventive subject matter can be used in greenhouse situations to greatly increase the growth rate of plants, especially in stimulating the growth of seedlings, for example with hydroponic/aeroponics systems' conductive pathways. Yet another use of a device of the inventive subject matter is in increasing the growth/metabolism of bacteria. Contemplated uses can range from wastewater treatment to methane production or even composting. Numerous existing bacterial bioreactors could be used in conjunction with a device of the inventive subject matter.

From a methods perspective, technology of the inventive subject matter can comprise self-contained probe units that are fit for use in conjunction with an existing or new bioreactor, for example, a fermentation tank.

FIGS. 2A-2D show test data from various tests conducted using device(s) of the inventive subject matter with an existing bioreactor. The devices were configured to administer different EPs to a solution reacted upon by the reactor to increase the fermentation rate of microbes in the nutrient solution. The Y-axis represents milliliters of displacement based on $CO_2$ output, while the X-axis represents a time in minutes. The numerical Y-value corresponding to each 30(n) minutes is listed below the X-axis.

Figure 3:
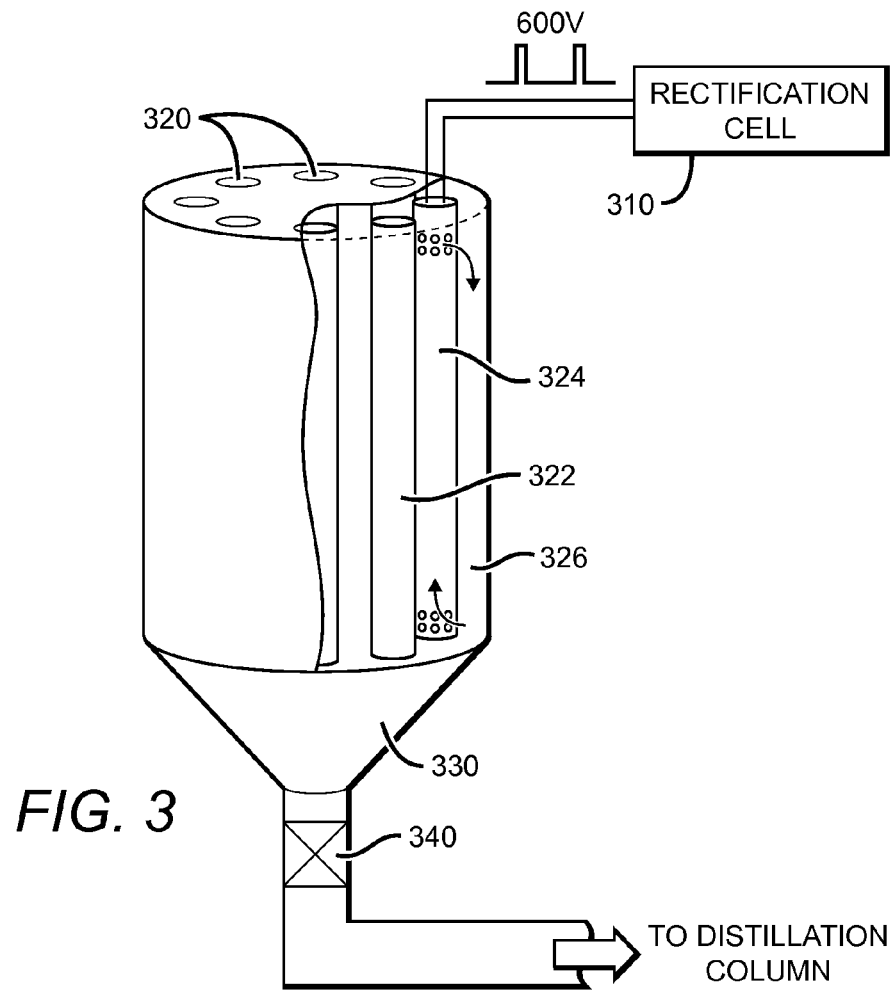
FIG. 3 is a partial cutaway schematic of a fermentation tank used in conjunction with a device or system of the inventive subject matter.
Figure 2A:
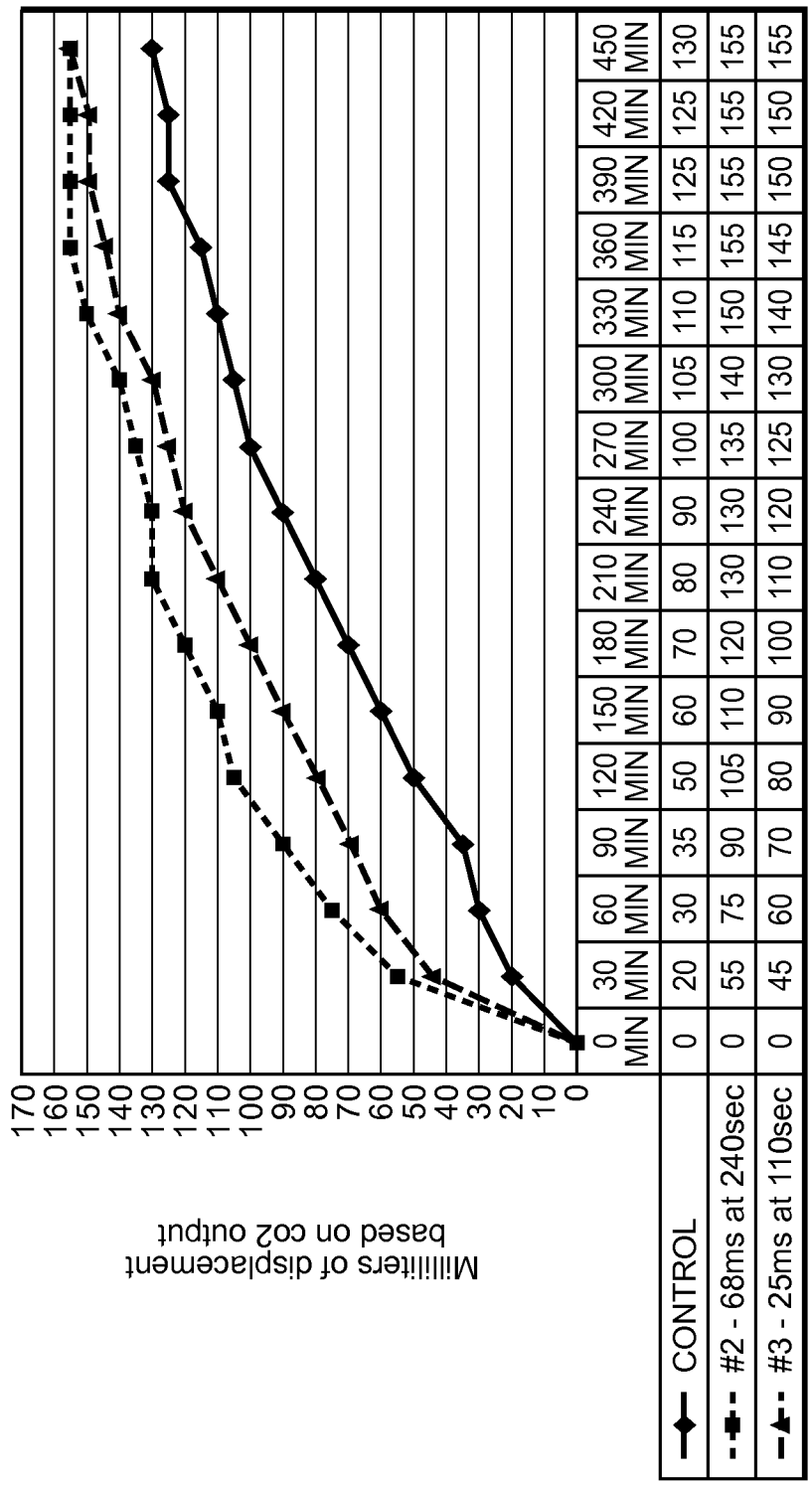
FIGS. 2A-D are graphs showing test data from tests conducted with different EPs.
Figure 2B:
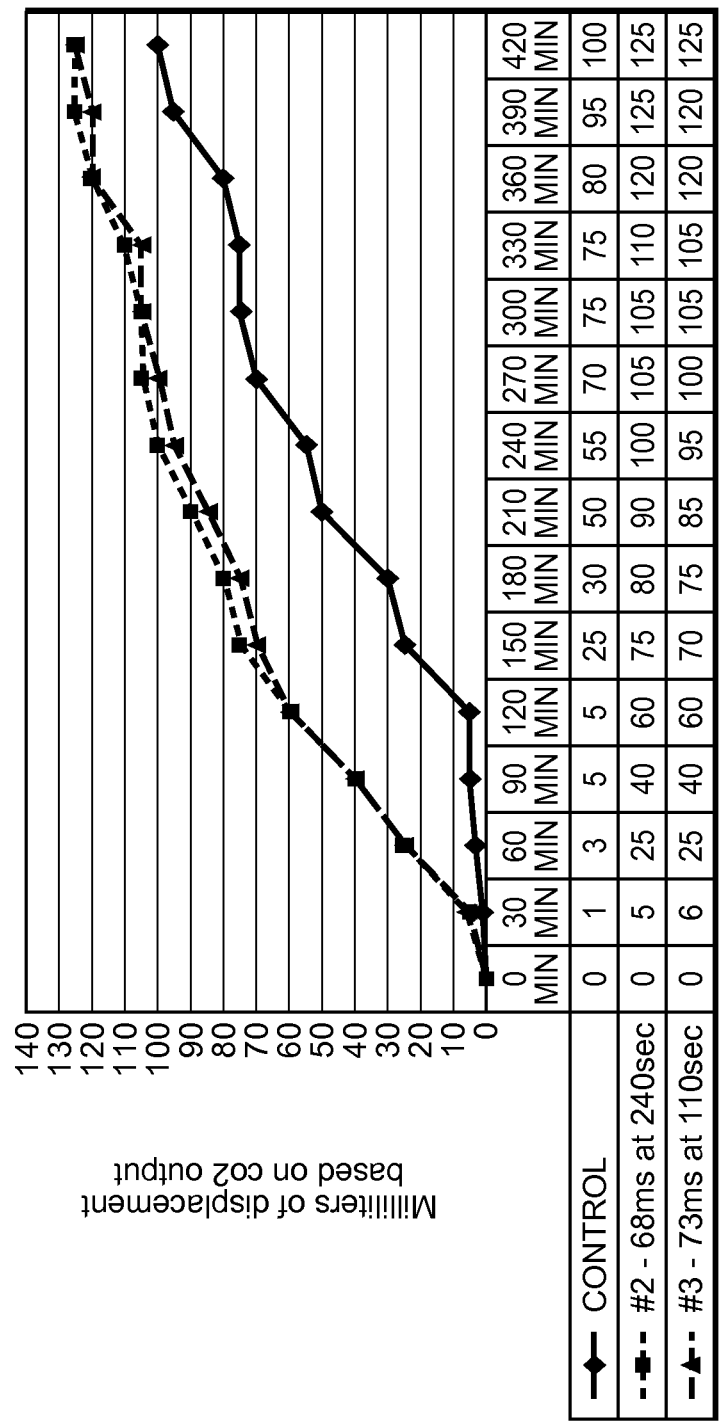
Figure 2C:
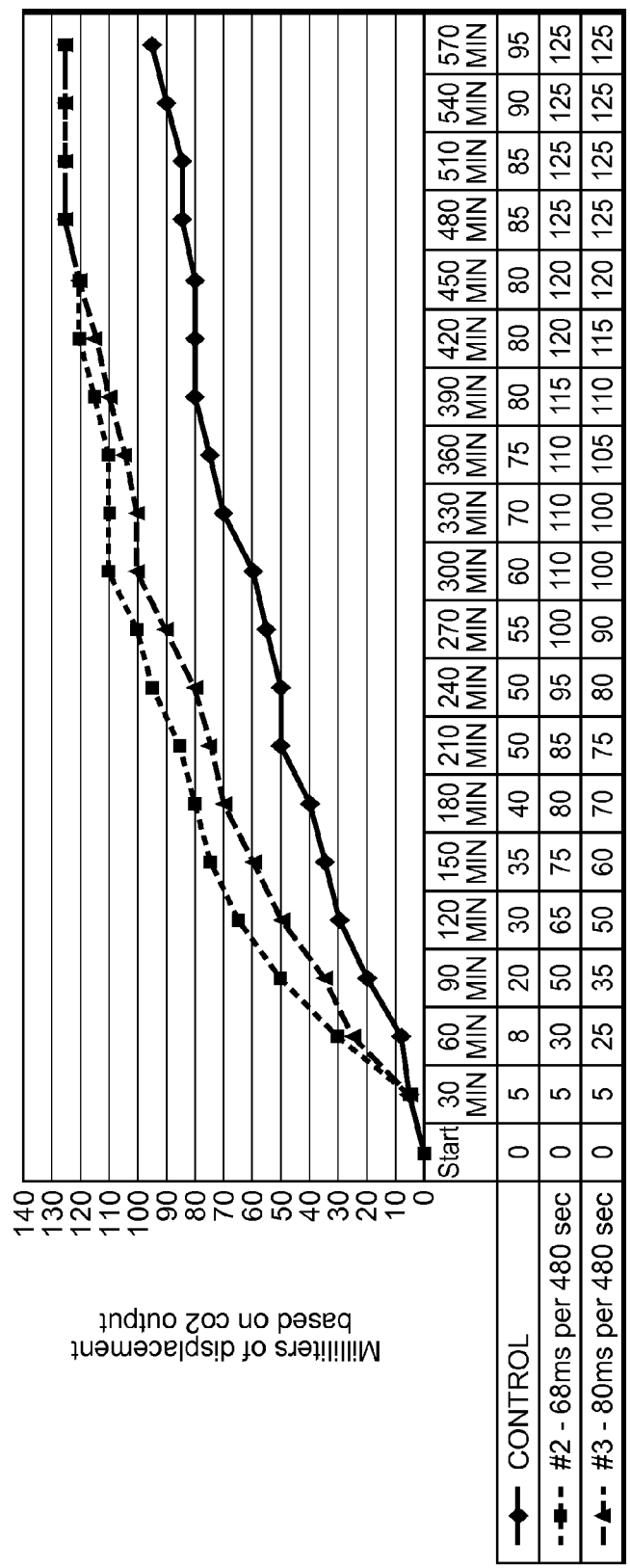
Figure 2D:
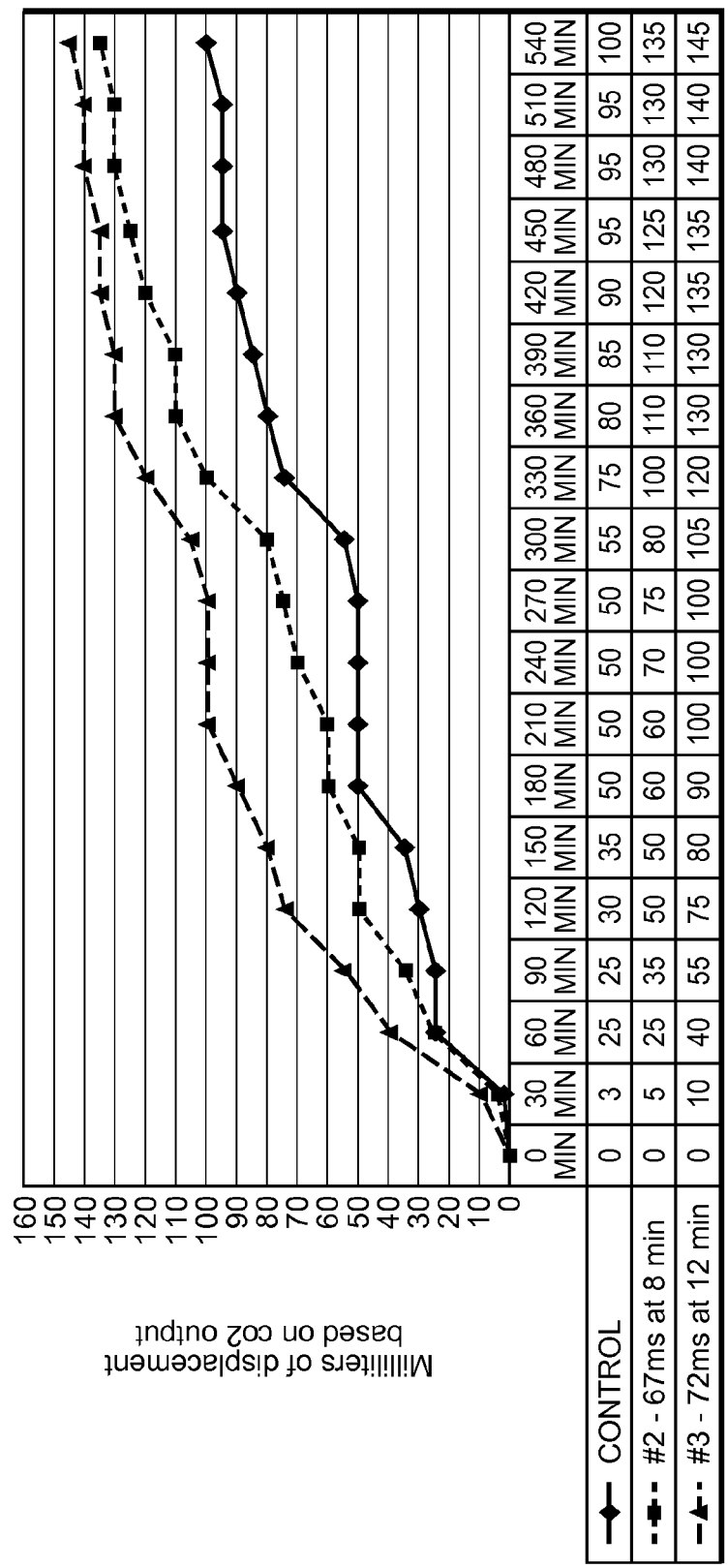

FIG. 3 shows a fermentation tank 330 used in conjunction with a system of the inventive subject matter, which comprises probes 320 (e.g., Dry EM Stimulator pulse probe 322, EM wet probe 324, etc.). Each probe (RFR) can be submerged in a solution 326 comprising at least one of water, yeast, and sugar. A rectification cell 310 can be configured (e.g., via one or more controls) to drive high voltage electric pulses (e.g., 600V, 800V, or even 1,000 or more V, etc.), have a short duration (e.g., 1 microsecond, 5 microseconds, 10 microseconds, etc.). A control can also be configured to allow operators to control a period between pulses (e.g., 5 minutes, 10 minutes, 5 minutes between a first and second pulse and 10 minutes between a second pulse and third pulse, etc.). The device can further comprise one or more pumps configured to direct at least a portion of the solution through an RFR at a particular rate, and in a selected direction. Contemplated solutions can comprise a slurry that includes at least one of water, a microbe, and cellulosic waste (e.g., a biofuel, etc.).

It is contemplated that the flow rate of the solution, the number of probes 320, and the stimulation of EPs from the probes can be scaled to optimize, or be used in conjunction with, any suitable bioreactor and process.

The fermentation tank 330 can be coupled to a drain valve 340 configured to allow a solution 326 to exit fermentation tank 330 and flow to a distillation column or other apparatus, for example, upon completion of a fermentation.

In one aspect of the inventive subject matter, the solution can be maintained at a suitable pH relative to the microorganisms used. For many microorganisms, a suitable pH is contemplated to be in the range of 6 to 8. In one aspect of the inventive subject matter, the solution can be maintained at a suitable temperature relative to the microorganisms used. For many microorganisms, a suitable temperature is contemplated to be in the range of 20 to 40° C.

The fermentation tank (e.g., 330) can advantageously be operated at a pressure of below 10 atm, below 5 atm or even below 2 atm. Especially preferred embodiments can operate at ambient (atmospheric) pressure.

Pulse driving circuitry (e.g., rectification cell 310) can be provided in a system to drive EPs at a frequency that was previously determined to be advantageous to a growth/metabolism of a type of microbe present in the solution.

Figure 4:
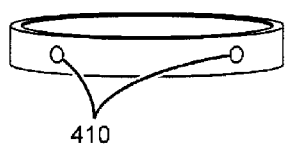
FIG. 4 is a perspective view of a probe locking collar of the inventive subject matter.

FIG. 4 shows a RFR/probe locking screw collar 400 of the inventive subject matter. The screw collar 400 provides a means for suspending the probes at least partially within a bioreactor, when desired. The collar further provides for quick and easy removal, replacement, or height adjustment of a probe. Setscrews or any other suitable collar locking mechanism (e.g., 410) of the collar can be tightened around a probe to lock it in place within a bioreactor.

Figure 5:
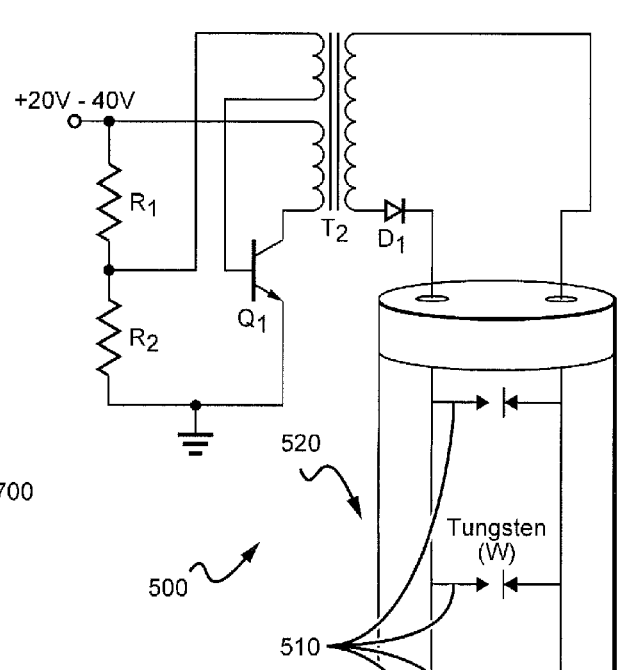
FIG. 5 is a schematic of an RFR of the inventive subject matter, with corresponding electrical circuit.

FIG. 5 shows one possible RFR of the inventive subject matter. Dry EM Stimulator Probe 500 consists of a watertight cylinder 520 within which a series of tungsten or other suitable metal electrodes are energized, providing a series of sparks between them, transcending up the length of the probe. These sparks produce EPs of a wide range of frequencies that can stimulate the growth/metabolism of microorganisms. Again, the power supply, the pulse driving circuitry and the controls can be integral to the probe itself.

The electrodes 510 can be disposed along a length of a probe 500 in any suitable configuration, for example, having a particular spacing (e.g., at a phi ratio).

Figure 6:
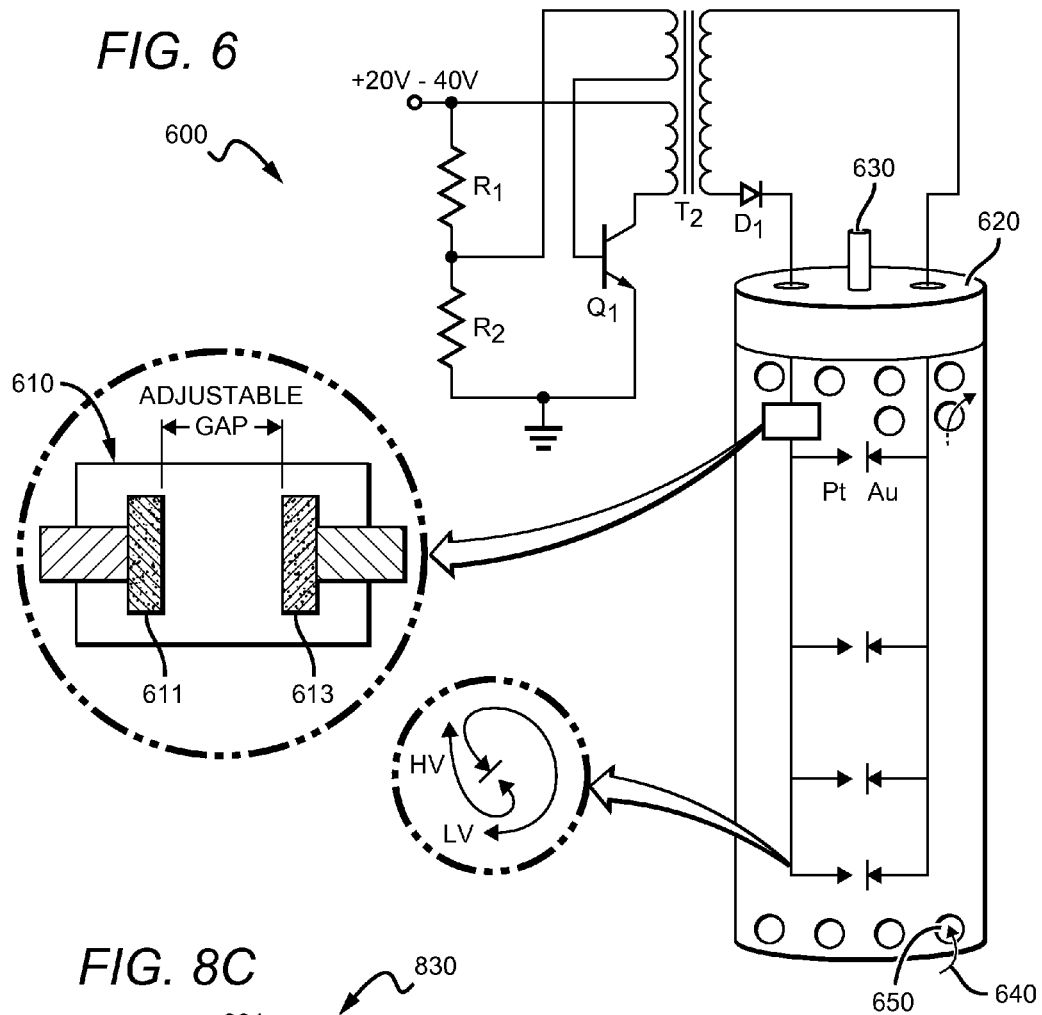
FIG. 6 is a schematic of another RFR of the inventive subject matter, with corresponding electrical circuit.

FIG. 6 shows another possible RFR of the inventive subject matter having a cylinder 620 and a vent 630. The EM Web Probe 600, like the probe of FIG. 5, can be submerged in a solution being treated 650 in a bioreactor. The probe comprises a plurality of flow holes at upper and lower ends in which the solution 650 can flow in and out of the pipe. This flow 640 can be directed or sped up via one or more pumps (e.g., an external pump). Electrodes are disposed along the inner length of the probe, and a high voltage rectification cell is disposed within the probe.

Where DC current is used, the anode preferably comprises, or is at coated with, gold or platinum and the cathode preferably comprises, or is coated with, gold or platinum. These metals are selected because of their nonreactivity and high electron shell configurations. Other suitable anode materials are contemplated to include platinum metal group (PMG) and transitional conductive metals, or any alloy thereof. Other suitable cathode materials are contemplated to include PMG and transitional conductive metals, or any alloy thereof.

The electrode chain can be mounted on two separate semi-circular assemblies, wherein rotation of these assemblies adjusts the distance between the submerged electrodes, allowing for optimization of a stimulation process. Again, the power supply, the pulse driving circuitry (e.g., rectification cell 610) and the controls can be integral to the probe itself.

Rectification cell 610 comprises first and second contacts (e.g., 611, 613), which are described in further detail below.

Figure 7:
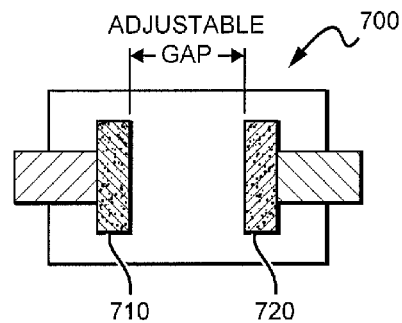
FIG. 7 is a schematic of a rectification cell of the inventive subject matter.

FIG. 7 shows a rectification cell 700 of the inventive subject matter. The rectification cell 700 can be disposed exterior to, or disposed interior to, a probe of the inventive subject matter. This rectification cell can provide a source of EPs that assists the stimulation of a fermentation process. A high voltage potential across two contacts (carbon foam impregnated with mercury, and aerogel impregnated with copper, etc.) 710 and 720 can create a spark between them. The spark(s) can provide a source of EP, and can be adjusted by changing the distance between the two contacts 710 and 720.

FIG. 8A-8D are examples of possible RFR and pump configurations. RFR 810 comprises a substantially straight tube having a length 816 and a lumen 815. Electrodes 812 are disposed between a first wall 813 and second wall 814 of the RFR 810. Pump 811 is configured to direct a flow of a solution in a particular direction (e.g., flow direction 818).

Figure 8A:
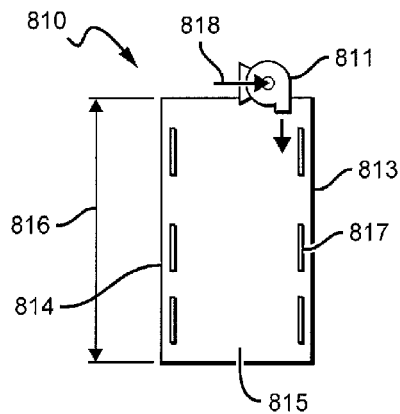
FIGS. 8A-D is a schematic of a selection of possible RFR shapes.
Figure 8B:
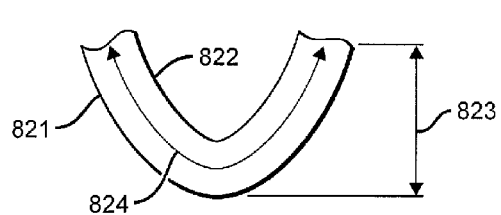

In FIG. 8B, RFR 820 comprises a curved shape having a first length 823 and a second length 824. The second length runs between first wall 821 and second wall 822 of RFR 820. A pump (not shown) pumps fluid through the device.

Figure 8C:
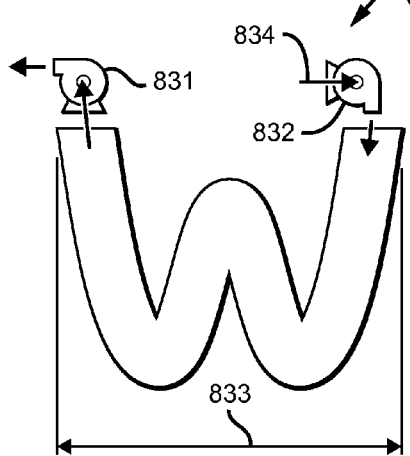

In FIG. 8C, RFR 830 comprises a multi-curved tube shape and is coupled with first pump 831 and second pump 832. In this embodiment, a solution can flow into RFR 830 in direction 834 as directed by second pump 832, then flow out of RFR 830 in direction 835 as directed by first pump 831. RFR 830 comprises a first length 833 and various other lengths (e.g., a length of a first wall, length of a second wall, length along a lumen, etc.).

Figure 8D:
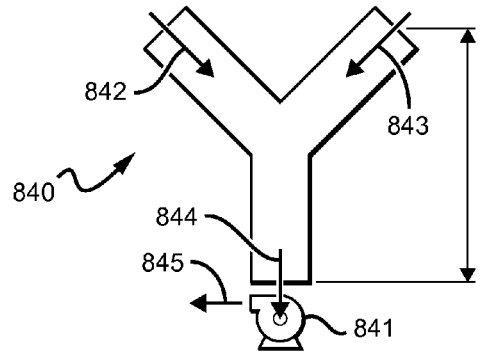

In FIG. 8D, RFR 840 comprises a substantially-Y shape and is coupled with pump 841, configured to direct a solution along flow directions 842, 843, 844 and 845. Pump 841 pumps fluid through the device. The lengths and other dimensions of each of the arms can be whatever is suitable to the application. While some possible configuration are described above, it should be appreciated that RFRs of any suitable size and shape are contemplated.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A flow tube reactor system for facilitating fermentation of a liquid within a first fermentation vat, comprising:
    a reactor tube having a lumen, and a length of at least 0.1 meter;
    a pulse driving circuitry that provides electrical pulses to an interior of the lumen at a pulse length and duty cycle effective to increase a fermentation rate of a microorganism;
    wherein the electrical pulses are produced at a plurality of electrodes placed along a length of reactor tube; and
    wherein the reactor tube is sized and dimensioned to be at least one of (a) submerged in a solution of the first fermentation vat, and (b) suspended in the first fermentation vat.

2. The reactor system of claim 1, wherein the reactor tube has a length of at least 1 meter.

3. The reactor system of claim 1, wherein the reactor tube has an inner diameter of at least 2 cm.

4. The reactor system of claim 1, wherein at least some of the plurality of electrodes are placed along the length of the reactor tube with an uneven spacing.

5. The reactor system of claim 4, wherein the uneven spacing approximates a phi spacing.

6. The reactor system of claim 4, wherein at least four of the plurality of electrodes have a progressively greater inter-electrode spacing along the length of the reactor tube.

7. The reactor system of claim 4, wherein the pulse driving circuitry drives the electrical pulses at a frequency of at least 10 kHz.

8. The reactor system of claim 4, wherein the pulse driving circuitry drives the electrical pulses at a frequency of at least 20 kHz.

9. The reactor system of claim 4, wherein the pulse driving circuitry drives the electrical pulses at a frequency previously determined to be advantageous to growth of a type of microbe present within the liquid.

10. The reactor system of claim 1, further comprising a second reactor tube having a lumen, and a length of at least 0.1 m, wherein the second reactor tube is sized and dimensioned to be at least one of (a) submerged in the solution of the fermentation vat, and (b) suspended in the fermentation vat.

11. The reactor system of claim 1, wherein the plurality of electrodes comprises a plurality of electrode pairs, and wherein a distance between at least one electrode pair of the plurality of electrode pairs is adjustable via at least one of a control and a rotation assembly coupled to the at least one electrode pair.

12. The reactor system of claim 1, wherein the reactor tube is further sized and dimensioned to be suspended in the first fermentation vat via at least one collar.

13. The reactor system of claim 12, wherein the at least one collar allows for an adjustment of a position of the reactor tube within the first fermentation vat.

14. A method of fermenting a fluid to produce a product, comprising:
    placing components of the fluid in a vat, at least one of the components comprising a microbe;
    suspending a flow tube in the vat; and
    operating the flow tube such that a portion of the fluid within the vat flows through the tube, and the tube provides electrical pulses via a plurality of electrodes to the fluid flowing within a lumen of the flow tube at a pulse length and duty cycle effective to increase a fermentation rate of the microbe.

15. The method of claim 14, further comprising maintaining a pH of the fluid no lower than 4 for at least one hour.

16. The method of claim 14, further comprising maintaining a temperature of the fluid no greater than 40° C. for at least one hour.

17. The method of claim 14, further comprising operating the vat at below 2 atm pressure.

18. The method of claim 14, further comprising pumping the fluid through the flow tube.

19. The method of claim 14, further comprising adjusting a pulse driving circuitry to drive the electrical pulses at a frequency previously determined to be advantageous to growth of a type of microbe present within the fluid.

20. The method of claim 14, wherein the microbe is a yeast.

21. The method of claim 14, wherein the microbe is a bacterium.

22. The method of claim 14, wherein the product comprises an alcoholic beverage.

23. The method of claim 14, wherein one of the components comprises a cellulosic waste.

24. The method of claim 14, wherein the product comprises ethanol.

25. The method of claim 14, wherein the fluid comprises a slurry that includes water and a cellulosic waste.

\* \* \* \* \*